United States Patent
Bornzin et al.

(10) Patent No.: US 9,427,594 B1
(45) Date of Patent: Aug. 30, 2016

(54) METHOD AND SYSTEM FOR TRACKING EVENTS OF INTEREST BETWEEN LEADLESS AND SUBCUTANEOUS IMPLANTABLE CARDIOVERTER DEVICES

(71) Applicant: PACESETTER, INC., Sylmar, CA (US)

(72) Inventors: Gene A. Bornzin, Simi Valley, CA (US); Laurence S. Sloman, West Hollywood, CA (US); John W. Poore, South Pasadena, CA (US); Yelena Nabutovsky, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/721,464

(22) Filed: May 26, 2015

(51) Int. Cl.
*A61N 1/00* (2006.01)
*A61N 1/372* (2006.01)
*A61N 1/365* (2006.01)
*A61N 1/375* (2006.01)

(52) U.S. Cl.
CPC ....... *A61N 1/37288* (2013.01); *A61N 1/36514* (2013.01); *A61N 1/3756* (2013.01)

(58) Field of Classification Search
CPC ..................... A61N 1/37288; A61N 1/36514; A61N 1/3756
See application file for complete search history.

(56) References Cited

U.S. PATENT DOCUMENTS

| | | |
|---|---|---|
| 8,744,572 B1 | 6/2014 | Greenhut et al. |
| 8,788,035 B2 | 7/2014 | Jacobson |
| 8,798,745 B2 | 8/2014 | Jacobson |
| 2013/0123872 A1* | 5/2013 | Bornzin ............ A61N 1/36592 607/17 |
| 2014/0107723 A1 | 4/2014 | Hou et al. |

* cited by examiner

*Primary Examiner* — George Manuel
(74) *Attorney, Agent, or Firm* — Theresa A. Raymer

(57) ABSTRACT

A distributed leadless implantable system and method are provided that comprise a leadless implantable medical device (LIMD). The LIMD comprises a housing having a proximal end configured to engage local tissue of interest in a local chamber, cardiac sensing circuitry to sense cardiac signals; and a controller configured to analyze the cardiac signals and, based thereon, to produce a near field (NF) event marker indicative of a local event of interest (EOI) occurring in the local chamber. The system and method further comprise a subcutaneous implantable medical device (SIMD). The SIMD comprises cardiac sensing circuitry to sense cardiac signals, a controller configured to identify a candidate EOI from the cardiac signals, and pulse sensing circuitry to detect the NF event marker from the LIMD. The SIMD controller is configured to declare the candidate EOI as a valid EOI or an invalid EOI based on the NF event marker.

24 Claims, 8 Drawing Sheets

METHOD AND SYSTEM FOR TRACKING EVENTS OF INTEREST BETWEEN LEADLESS AND SUBCUTANEOUS IMPLANTABLE CARDIOVERTER DEVICES

Embodiments herein generally relate to implantable medical devices, and more particularly to coordination of operation of separate implantable devices.

BACKGROUND OF THE INVENTION

Currently, subcutaneous implantable medical devices (SIMD) are provided for a variety of cardiac applications. The SIMD include a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker, cardioversion and/or defibrillation functionality.

Recently, small sized devices have been proposed for intra-cardiac implant within the heart. These devices, termed leadless pacemakers or leadless implantable medical devices (LIMDs), are typically characterized by the following features: they are devoid of leads that pass out of the heart to another component, such as a pacemaker can outside of the heart; they include electrodes that are affixed directly to the can of the device; the entire device is attached to the heart; and the device is capable of pacing and sensing in the chamber of the heart where it is implanted.

LIMDs that have been proposed thus far offer limited functional capability. These LIMDs are able to sense in one chamber and deliver pacing pulses in that same chamber, and thus offer single chamber functionality. For example, an LIMD that is located in the right atrium would be limited to offering AAI mode functionality. An AAI mode LIMD can only sense in the right atrium, pace in the right atrium and inhibit pacing function when an intrinsic event is detected in the right atrium within a preset time limit. Similarly, an LIMD that is located in the right ventricle would be limited to offering VVI mode functionality.

Various limitations and tradeoffs exist when deciding whether to implant an SIMD or an LIMD. An LIMD represents a new leadless technology that may afford an opportunity to mitigate risks associated with lead failures and replacements. A leadless SIMD has also been created for the same lead issues and cosmetic reasons.

Transvenous pacemakers provide single, dual chamber and CRT/BiV pacing modalities while first generation LIMDs are single chamber right ventricular only devices. Further, first generation S-ICDs have been reported to be prone to T-wave over-sensing especially in the younger and pediatric patient groups. It has been shown that atrial-ventricular (AV) synchronous LV pacing may be desirable over RV pacing alone. In many cases, LV pacing provides the same benefits as cardiac resynchronization therapy CRT bi-ventricular pacing.

A need remains for a unified system that delivers AV synchronous pacing to the left ventricle as well as high voltage therapy.

SUMMARY

In accordance with embodiments herein, a distributed implantable system is provided that comprises a leadless implantable medical device (LIMD) configured to be implanted entirely within the heart and to deliver a pacing therapy. The LIMD comprises a housing having a proximal end configured to engage local tissue of interest in a local chamber, electrodes located along the housing, LIMD cardiac sensing circuitry to sense cardiac signals; and a LIMD controller configured to analyze the cardiac signals and, based thereon, to produce a near field (NF) event marker indicative of a local event of interest (EOI) occurring in the local chamber. The system further comprises a subcutaneous implantable medical device (SIMD) to be located proximate to the heart and configured to deliver an arrhythmia therapy. The SIMD comprises SIMD cardiac sensing circuitry to sense cardiac signals, a SIMD controller configured to identify a candidate EOI from the cardiac signals, and pulse sensing circuitry to detect the NF event marker from the LIMD. The SIMD controller is configured to declare the candidate EOI as a valid EOI or an invalid EOI based on the NF event marker.

The SIMD controller is configured to track valid EOIs based on NF event markers to avoid over sensing candidate EOIs as valid EOIs. Optionally, when the event of interest corresponds to an R-wave of the cardiac signal, the SIMD controller may identify both an R-wave and a T-wave from the cardiac signals as candidate events of interest. The SIMD controller validates the R-wave as the valid event of interest and the T-wave as the invalid event of interest based on the NF event marker. Optionally, the LIMD generates the NF event marker contemporaneous in time with the R-wave, representing the event of interest. The SIMD controller utilizes the NF event marker to avoid tracking the T-wave in the cardiac signal as another R-wave.

Optionally, the LIMD controller produces, as the NF event marker, at least one of a pacing pulse and a communications pulse. Optionally, the SIMD cardiac sensing circuitry further comprises a discriminator configured to only pass cardiac signals that exceed a select sensing threshold. Optionally, the LIMD controller analyzes the cardiac signal for noise reversion and enters an asynchronous pacing mode when detecting the noise reversion. The LIMD controller generates a mode switching pulse, and the SIMD controller recognizes the mode switching pulse to indicate that the LIMD is entering the asynchronous pacing mode. Optionally, the SIMD automatically adjusts at least one of a sensing vector, sensing threshold and AV refractory interval based on a number of the candidate EOIs that are declared to be invalid EOIs due to a lack of corresponding NF event markers. Optionally, when the SIMD detects an excess plurality of the NF event markers within a predetermined period of time, the SIMD enters a marker-disable mode and disregards the NF event markers when declaring candidate EOIs as valid or invalid EOIs.

In accordance with embodiments herein, a distributed implantable system is provided that comprises a leadless implantable medical device (LIMD) configured to be implanted entirely within a local chamber of the heart; and a subcutaneous implantable cardioverter device (SIMD) configured to deliver an arrhythmia therapy. The SIMD comprises SIMD cardiac sensing circuitry to sense cardiac signals, and a SIMD controller configured to analyze the cardiac signals and based thereon, to produce a far field (FF) event marker indicative of a remote event of interest (EOI) occurring in a remote chamber that differs from the local chamber. The LIMD comprises a housing having a proximal end configured to engage local tissue of interest in the local chamber, electrodes located along the housing, LIMD cardiac sensing circuitry to sense cardiac signals, and LIMD pulse sensing circuitry to detect the FF event marker. The LIMD further comprises a LIMD controller configured to initiate an interval timer based on detection of the FF event marker and based thereon, to delivery a pacing pulse.

Optionally, the LIMD controller analyzes the cardiac signal for an intrinsic near field (NF) event, and delivers the pacing pulse when the intrinsic NF event is not present in the cardiac signal before the interval timer times out. Optionally, the local chamber is a ventricle and the remote EOI represents a P-wave. The SIMD transmits the FF event marker to direct the LIMD to initiate a PV interval timer as the interval timer. The LIMD delivers a ventricular pacing pulse when the LIMD is not inhibited by an intrinsic R-wave representing the intrinsic local event. Optionally, the SIMD controller declares an atrial event to occur as the remote EOI in response to detecting an atrial event that exceeds a P-wave sense threshold within a P-wave timing window.

The LIMD controller may be configured to analyze the cardiac signals and, based thereon, produce a near field (NF) event marker when a local EOI occurs in the local chamber. The SIMD controller may be configured to set a P-wave timing window based on receipt of the NF event marker, the SIMD controller searching for an atrial event during the P-wave timing window.

In accordance with embodiments herein, a method is provided for coordinating operation of a distributed implantable system having a leadless implantable medical device (LIMD) to be implanted entirely within a local chamber of the heart and to deliver a pacing therapy and having a subcutaneous implantable medical device (SIMD) to be located proximate to the heart and to deliver an arrhythmia therapy. The method comprises programming the LIMD to sense and analyze cardiac signals and, based thereon, to produce a near field (NF) event marker indicative of a local event of interest (EOI) occurring in the local chamber. The method configures the SIMD to sense cardiac signals and to sense the NF event marker from the LIMD; and programs the SIMD to identify a candidate EOI from the cardiac signals and to declare the candidate EOI as a valid EOI or an invalid EOI based on the NF event marker.

Optionally, the method declares, at the SIMD, the candidate EOI to be a valid EOI when the NF event marker is detected temporally contemporaneous with occurrence of the candidate EOI. Optionally, the method further comprises programming the SIMD controller to avoid over sensing candidate EOIs as valid EOIs by tracking valid EOIs based on the NF event markers. The local EOI may correspond to an R-wave, with the method identifying both an R-wave and a T-wave from the cardiac signals as candidate EOIs, and declaring the R-wave as the valid EOI and the T-wave as the invalid EOI based on the NF event marker.

In accordance with embodiments herein, a method is provided for coordinating operation of a distributed implantable system having a leadless implantable medical device (LIMD) to be implanted entirely within a local chamber of the heart to deliver a pacing therapy and having a subcutaneous implantable medical device (SIMD) to be located proximate to the heart and to deliver an arrhythmia therapy. The method comprises programming the SIMD to sense and analyze cardiac signals and, based thereon, to produce a far field (FF) event marker indicative of a remote event of interest (EOI) occurring in a remote chamber different from the local chamber. The method configures the LIMD to sense cardiac signals and to sense the FF event marker from the SIMD; and initiates an interval timer, at the LIMD, based on detection of the FF event marker. The method configures the LIMD to deliver a pacing pulse based on the interval timer.

Optionally, the method analyzes the cardiac signals sensed by the LIMD for an intrinsic near field (NF) event, and delivers the pacing pulse when the intrinsic NF event is not present in the cardiac signal before the interval timer times out. Optionally, the local chamber is a ventricle and the remote EOI represents a P-wave. The method transmits the FF event marker from the SIMD to direct the LIMD to initiate a PV interval timer as the interval timer, and configures the LIMD to deliver a ventricular pacing pulse when the LIMD is not inhibited by an intrinsic R-wave before the PV interval timer times out.

BRIEF DESCRIPTION OF THE DRAWINGS

FIG. 1 illustrates a graphical representation of a heart with an implantable medical system located therein in connection with providing pacing therapy, cardiac rhythm management (CRP) therapy and the like.

DETAILED DESCRIPTION

In accordance with embodiments herein, methods and systems are provided to reliably sense physiologic behavior of the heart and provide appropriate therapies utilizing a leadless system. Embodiments herein avoid certain difficulties experienced by traditional subcutaneous implantable medical devices, such as over sensing of certain events of interest, such as P-waves.

In accordance with embodiments herein, an SIMD senses event of interest, such as P-waves, using a composite electrogram that is received by the SIMD over one or more select sensing vectors. An LIMD senses R-waves using one or more local bipolar vectors. The SIMD and LIMD cooperate to track events of interest such as by utilizing the SIMD to sense P-waves associated with atrial activity. Based on the sensed P-waves, a PV interval timer is initiated and the LIMD is managed to deliver a pacing therapy when a related event of interest, such as an R-wave is not sensed within the PV interval.

Figure 1:
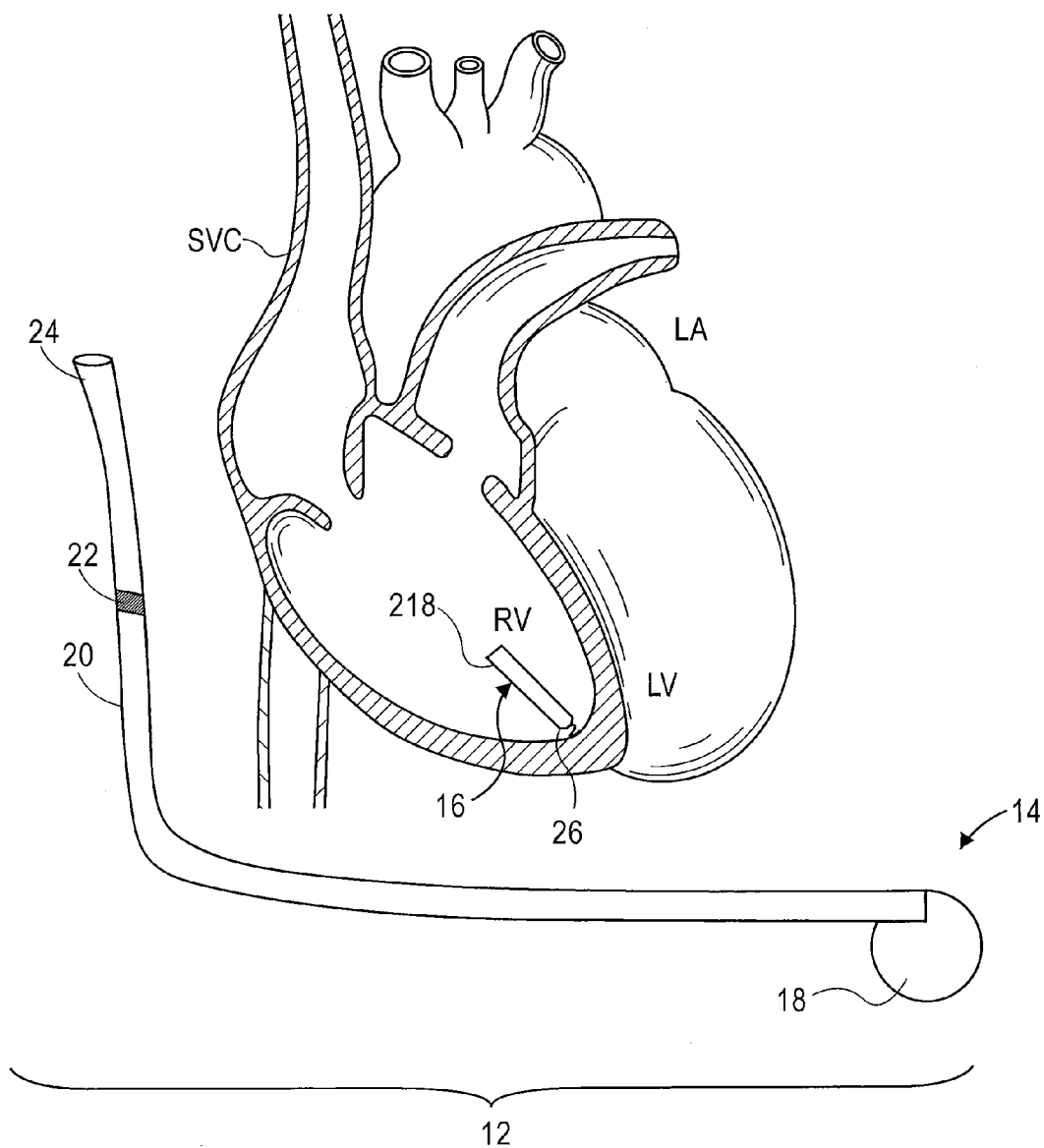

FIG. 1 illustrates a graphical representation of a heart with an implantable medical system 12 to provide pacing therapy, cardiac resynchronization therapy (CRT) as well as general arrhythmia therapy. The system 12 includes a first leadless implantable medical devices (LIMD) 16 configured to be implanted entirely within a corresponding first chamber of the heart. The system 12 also includes a subcutaneous implantable medical device (SIMD) 14 configured to be implanted in a subcutaneous area exterior to the heart.

In the example of FIG. 1, the LIMD 16 is implanted in the right ventricle. Optionally, additional LIMDs may be implanted in the left atrium and/or the left ventricle. Alternatively, the LIMD 16 may be implanted in other chambers and/or other positions exterior to the heart. For example, the LIMD 16 may be implanted in the right atrium, left atrium, or left ventricle. Optionally, more than one LIMD 16 may be utilized with each LIMD 16 positioned in a different chamber of the heart. The LIMD 16 is configured to deliver various therapies, such as pacing therapy, antitachycardia pacing therapy and the like.

In the example of FIG. 1, the SIMD 14 is positioned in a subcutaneous area. The subcutaneous implantable cardioverter-defibrillator is a device that does not require insertion of a transvenous lead. Rather, the SIMD includes subcutaneous pulse generator that may be implanted in the left lateral chest and a subcutaneous left parasternal lead-electrode. Optionally, the SIMD 14 may be positioned in a different subcutaneous area, such as proximate to the lower apex of the left ventricle and/or right ventricle. The SIMD 14 is configured to deliver various arrhythmia therapies, such as pacing therapy, antitachycardia pacing therapy, cardioversion therapy, defibrillation therapy and the like. Optionally, the LIMD 16 and SIMD 14 may deliver the same or different types of therapies, based upon device longevity, energy storage and other design characteristics.

The SIMD 14 includes a housing 18 having a header configured to be connected to a lead 20. The lead 20 includes one or more electrodes 22, 24 positioned along a length thereof. The housing 18 is also configured to operate as an electrode. The electrodes 22, 24 and the housing 18 are configured to perform sensing (along one or more sensing vectors) and to deliver various types of therapy. The lead 20 is positioned such that the electrodes 22 and 24 are positioned proximate to (but outside of) various regions or chambers of the heart. In the example of FIG. 1, the SIMD 14 is positioned proximate to the apex of the LV, while the electrode 22 is positioned at an intermediate point along the LV and the electrode 24 is positioned proximate the LA. Optionally, the SIMD 14 and lead 20 may be positioned in alternative locations and include alternative numbers of electrodes. Optionally, the SIMD 14 may be configured to operate without any lead 20 connected thereto. For example, the housing 18 of the SIMD 14 may include one or more electrically separate electrodes, where one combination of electrodes cooperates cooperate to perform sensing and the same or a different combination of electrodes cooperates to deliver therapy.

The LIMD 16 has a housing 28 with a proximal end 26 that is configured to engage local tissue in the right ventricle. Electrodes (not illustrated in FIG. 1) may be located along the housing 28 at various positions and combinations. The internal electrical components and electrodes may be implemented as described in U.S. Publication No. 2014/0107723, which is expressly incorporated herein by reference in its entirety.

As explained hereafter, the system 12 provides a distributed leadless pacing system that coordinates AV synchronous P-wave tracking between the LIMD 16 and SIMD 14. The distributed system 12 has one or more LIMDs 16 and one or more SIMDs 14 that operate as separate therapy delivery devices. The LIMD 16 and SIMD 14 include at least two types of sensing configurations, namely a cardiac event sensing channel tuned to detect intrinsic and/or paced cardiac events. For example, the cardiac event sensing channel, for an atrial pacing device, may be tuned and function to sense P-waves or paced events delivered in the atrium. A ventricular pacing device may be tuned and function to sense R-waves or paced events delivered in the ventricle over the cardiac event sensing channel. The LIMD 16 and SIMD 14 also include a marker sensing channels tuned to detect event markers. For example, the LIMD 16 may tune the marker sensing channel to detect event markers from the SIMD 14, and vice versa.

Figure 2:
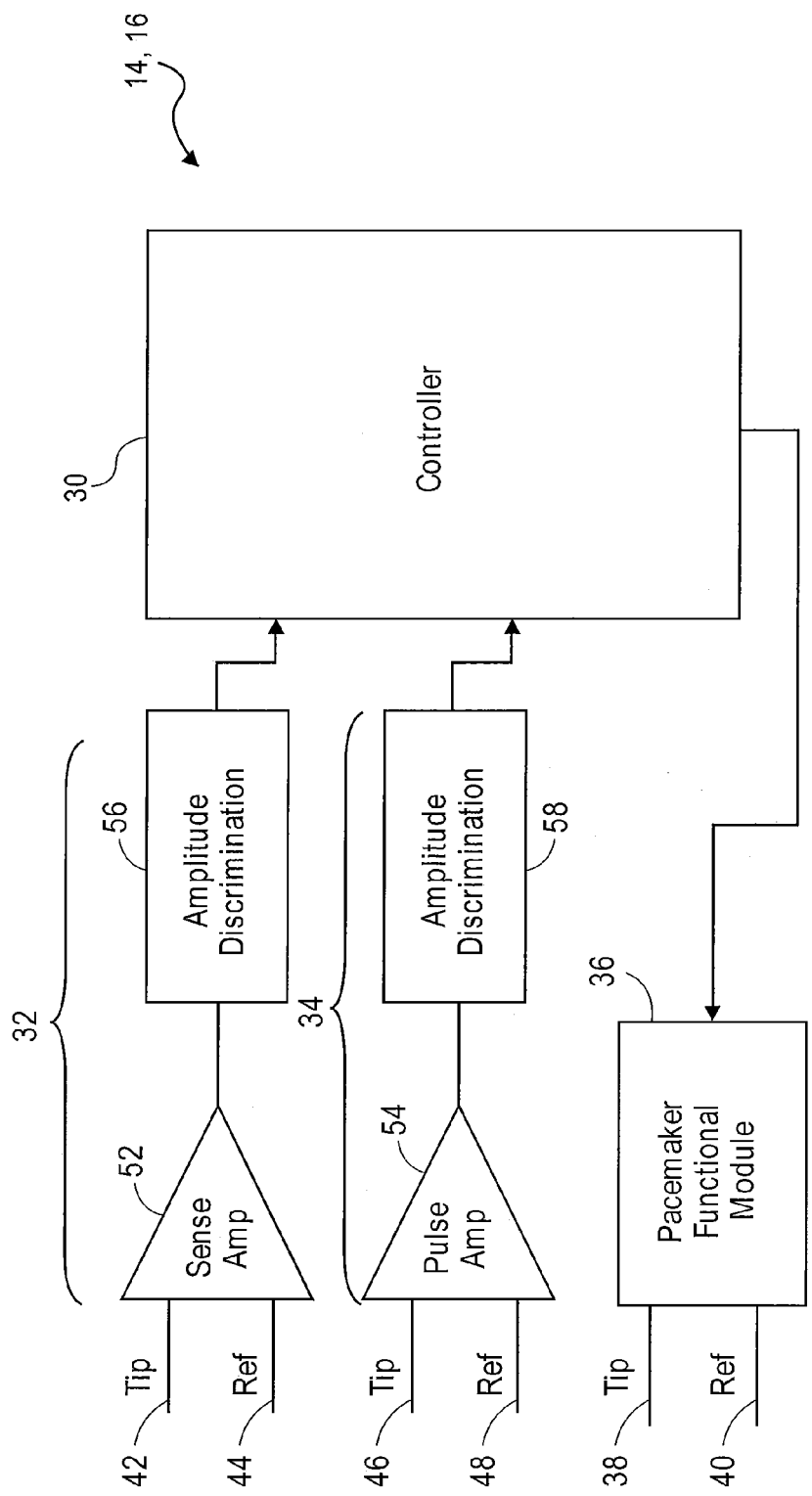
FIG. 2 illustrates a simple block diagram of at least a portion of the circuitry within an LIMD or SIMD in accordance with an embodiment herein.

FIG. 2 illustrates a simple block diagram of at least a portion of the circuitry within an LIMD 16 and SIMD 14. The SIMD 14 and LIMD 16 each include a controller 30 that is coupled to cardiac sensing circuitry 32 and pulse sensing circuitry 34. The controller 30 also utilizes or communicates with various other electronic components, firmware, software and the like that generally perform sensing and pacing functions (as generally denoted by a pacemaker functional block 36). While the examples herein are provided for pacing and defibrillation functions, the same distributed SIMD and LIMD could be programmed to perform antitachycardia pacing, cardiac rhythm therapy and the like. The cardiac sensing circuitry 32 is configured to detect intrinsic and paced cardiac events. The pulse sensing circuitry 34 is configured to detect event markers. The sensing circuitry 32 and 34 may be tuned in different manners based upon various characteristics, such as whether the sensing circuitry 32, 34 is listening for a near field (NF) or far field (FF) signals and the nature of the signal being sensed (e.g., a far field cardiac signal, a far field event marker, a near field cardiac signal, a near field event marker).

The event markers originate from an LIMD 16 and/or SIMD 14 that is located in a remote and different location from the receiving LIMD 16 or SIMD 14. The event markers have a predetermined pattern configured to indicate that an event of interest has occurred in the remote chamber. The pulse sensing circuitry 34 may be tuned in part based on the predetermined pattern expected in incoming event markers. The event of interest may represent a physiologic event, either intrinsically or externally induced (e.g., paced). The event of interest may also represent a non-physiologic action, such as the initiation or termination of a timer as used in connection with various operations of a pacemaker, and the like.

The controller 30 is configured to analyze incoming intrinsic and/or paced cardiac events (as sensed over the cardiac sensing circuitry 32). Based on this analysis, the controller 30 in the LIMD 16 performs various pacemaker related actions, such as setting or ending timers, recording data, delivery of therapy and the like. The controller 30 of the SIMD 14 performs various cardioversion/defibrillation related functions. At least the controller 30 of the LIMD 16 produces and outputs one or more event markers from the electrodes. In the example of FIG. 2, inputs 38 and 40 represent output terminals that are coupled through a switching circuit (in the functional module 36) to corresponding electrodes on the housing of the LIMD 16 and/or lead/housing of the SIMD 14.

Inputs 42-48 are provided to the cardiac and pulse sensing circuitry 32 and 34. By way of example, with reference to LIMD 16, inputs 42 and 44 may be coupled to tip and reference electrodes that supply sensed signals to a sensing amplifier 52. Inputs 46 and 48 may be coupled to the same or different tip and reference electrodes to provide sensed signals to a pulse amplifier 54. An output of the sensing amplifier 52 is supplied to amplitude discriminator 56, while an output of the pulse amplifier 54 is supplied to amplitude discriminator 58. Outputs of the amplitude discriminators 56 and 58 are then provided to the controller 30 for subsequent analysis and appropriate actions. With reference to the SIMD 14, the inputs 42 and 44 may be coupled to various combinations of the electrodes 22, 24 and the electrode formed by the housing 18.

By way of example, the sensing amp 52 and discriminator 56 may be tuned to perform NF or FF sensing and have programmable or automatic blanking periods. The blanking period is set to avoid sensing unwanted events at the sensing amp 52. For example, when the LIMD 16 represents a ventricular device, the sensing amp 52 and discriminator 56 may be tuned or configured to sense R-waves occurring in the local ventricle. Hence, the amp 52 may be programmed to a select gain, while the discriminator 56 is programmed to only pass signals that exceed a select sensing threshold. Optionally, the discriminator 56 may include a band pass, low pass or high pass filter set to only pass signals within a select frequency range. The amp 52 and/or discriminator 56 may have a low pass frequency (e.g., 10-120 Hz). The gain, threshold and/or pass band may be adjusted for atrial versus ventricular devices.

The pulse amplifier 54 and amplitude discriminator 58 are configured to detect select communications pulses having one or more known predetermined formats. For example, the gain of the amp 54 and threshold of the discriminator 58 may be set to pass only signals below a select pulse maximum threshold and/or pulses having a select duration. Optionally, the discriminator 58 may include a band pass, low pass or high pass filter set to only pass pulses within a select frequency range. The amp 54 and/or discriminator 58 may have a high pass frequency (e.g., 500 Hz-10 KHz). The pulse amp 54 and amplitude discriminator 58 may also be configured to sense pacing pulses delivered in the local and/or remote chambers. The communications pulses sensed by the pulse amp 54 and amplitude discriminator 58 represent event markers that are delivered to the controller 30 and used to indicate different events of interest (e.g., physiologic and non-physiologic events or actions). As explained herein, the controller 30 then takes appropriate action, depending upon the situation.

Optionally, a single amplifier may be used in place of amps 52 and 54, thereby detecting low and high frequency signals. An output of the single amp may be coupled to a low pass filter in parallel with a high pass filter that separate the low and high frequency components, respectively, namely the cardiac events and the communications pulses.

As used throughout, the terms "near field", "far field", "local" and "remote" shall be used from the perspective of the LIMD 16. Accordingly, the LIMD 16 will sense local events of interest in the near field that occur in the local chamber, in which the LIMD 16 is implanted. As an example, when the LIMD 16 is implanted in a ventricle, the local chamber constitutes the corresponding ventricle, and the near field corresponds to the same ventricle, while the far field corresponds to one or both atrium and may represent the opposite ventricle. The SIMD 14 (and sensing electrodes) are located outside of the heart and accordingly, the cardiac signals sensed by the SIMD 14 are not readily characterized as near field or far field relative to the SIMD. Also, the SIMD 14 is not readily characterized to have a local chamber or a remote chamber. Instead the SIMD 14 senses signals in the "Far Field" of the LIMD 16 and, from the perspective of the LIMD 16.

As explained herein, the LIMD and SIMD generate various event markers to be sensed by the other one of the SIMD and LIMD. For example, the LIMD generates near field event markers indicative of a local event of interest (EOI) occurring in the local chamber (the chamber where the LIMD is implanted), such as an R-wave or T-wave. The SIMD generates far field event markers indicative of a remote event of interest (EOI) occurring in a remote chamber that differs from the local chamber. For example, the remote EOI may represent a P-wave occurring in an atrium that is remote from a ventricle where the LIMD is implanted.

The event markers may be constructed as marker pulses that have various predetermined shapes, amplitudes, pulse widths, pulse patterns and the like. Different pulse formulations may be assigned different meanings to instruct receiving atrial or ventricular device to take difference actions. The pulse amplitude may be below a capture threshold that might otherwise achieve capture of heart tissue. The event markers may constitute or be embedded within pacing pulses. Additionally or alternatively, the event markers may be constructed as communications pulses or communications data packets.

Figure 3A:
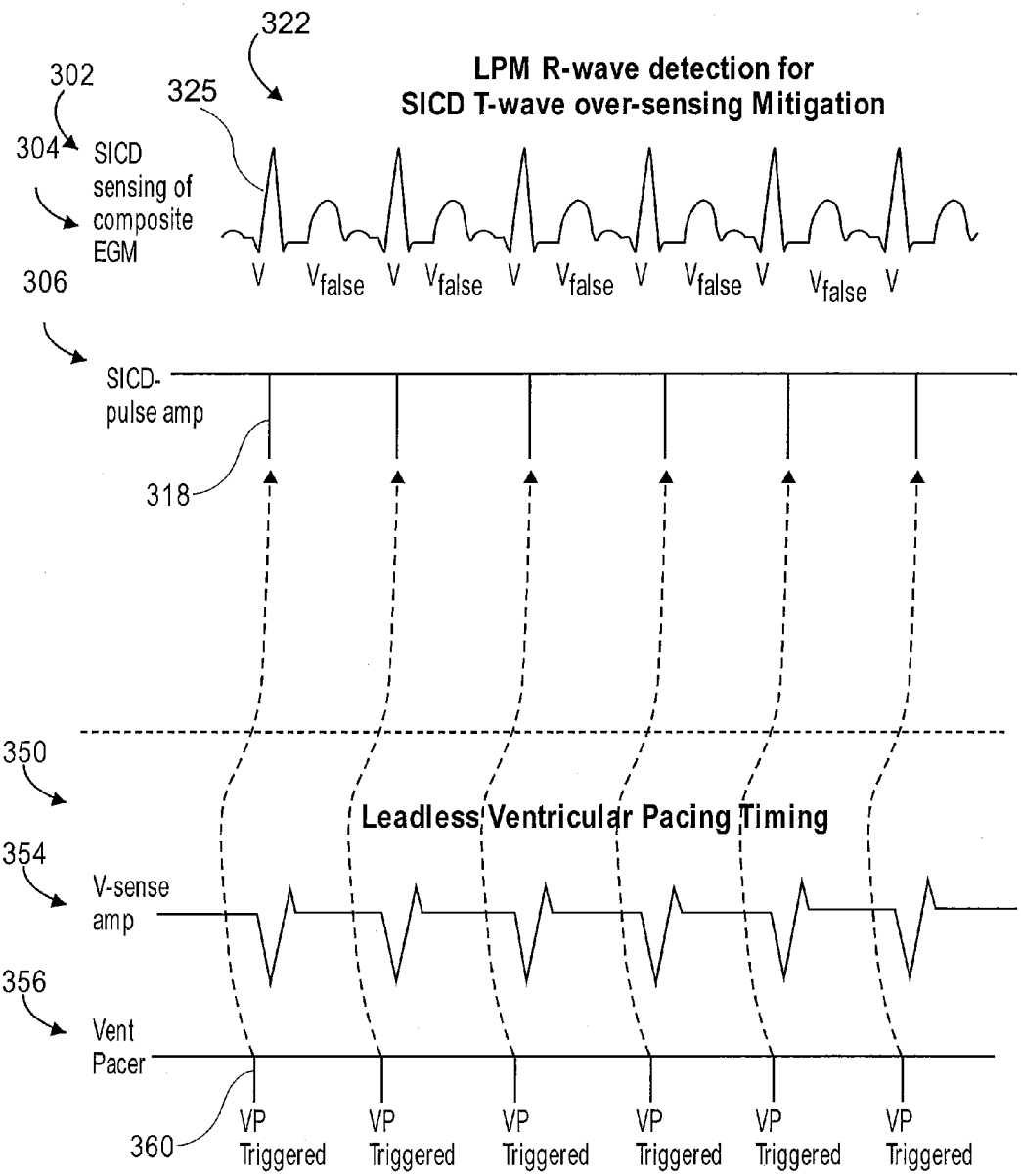
FIG. 3A illustrates an SIMD timing diagram and an LIMD timing diagram in accordance with an embodiment herein.
Figure 3B:
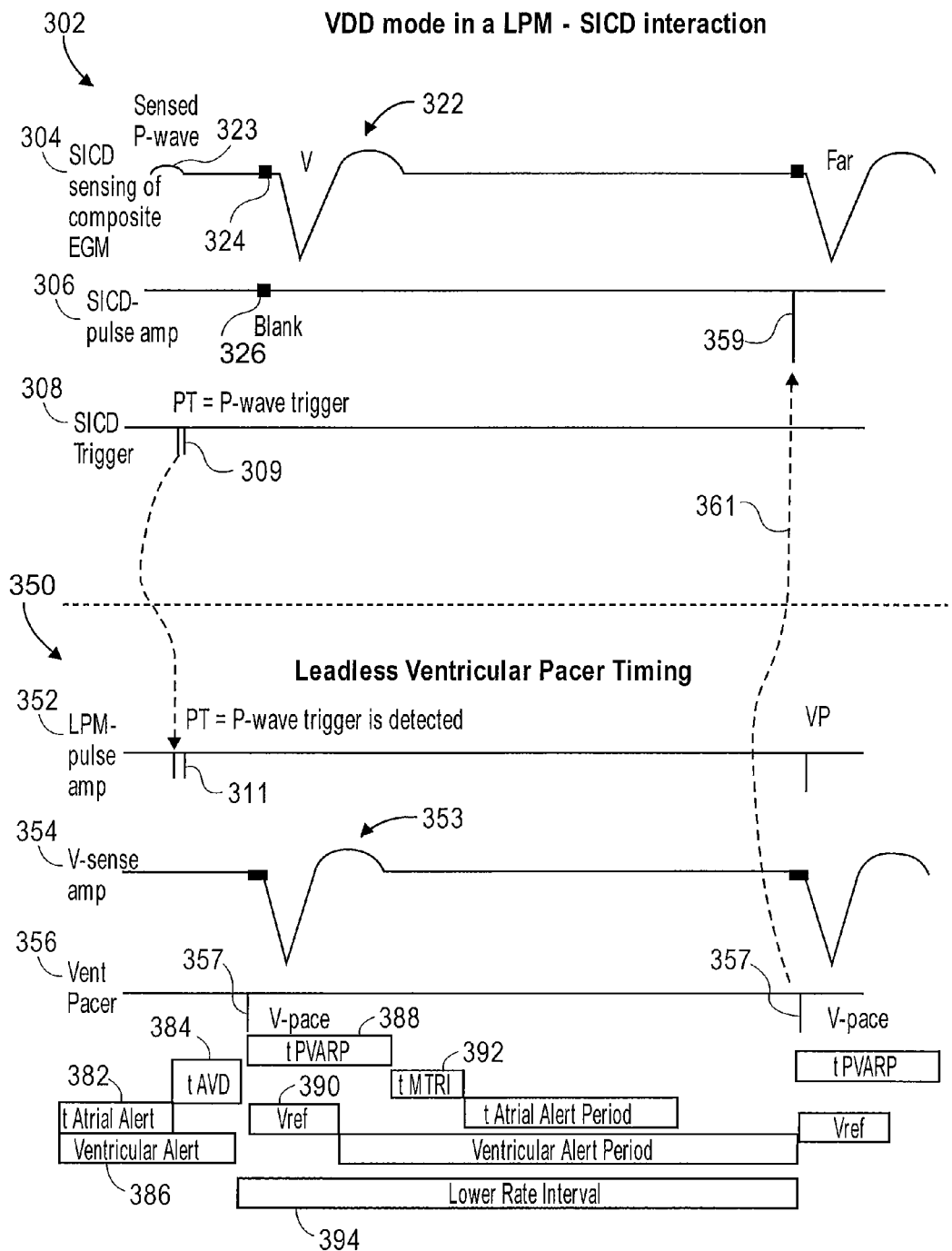
FIG. 3B illustrates the timing diagram information of FIG. 3A, along with additional timing information in accordance with an embodiment herein.
Figure 3C:
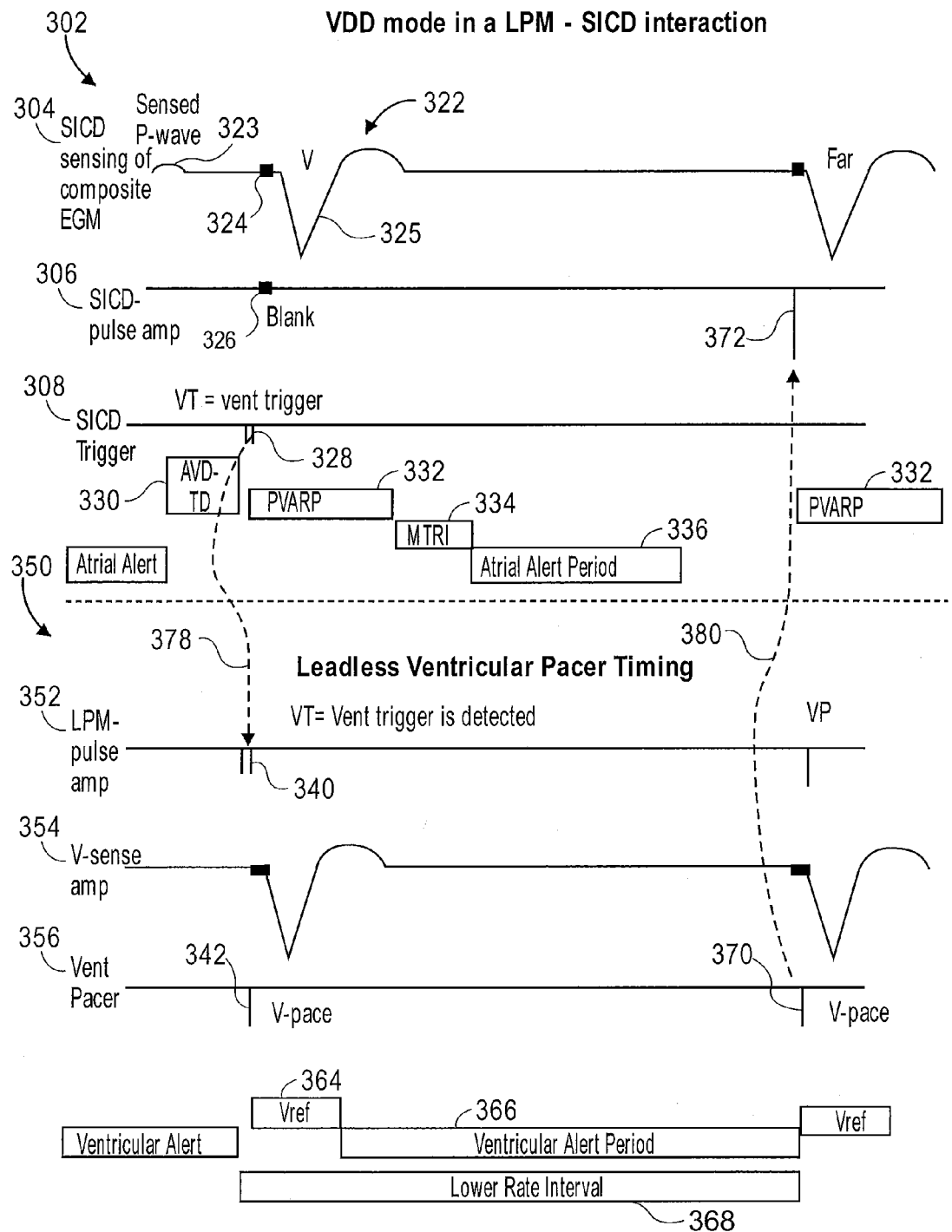
FIG. 3C illustrates the timing diagram information of FIG. 3A, along with additional timing diagram information in accordance with an embodiment herein.

Next, the discussion is provided in connection with a series of timing diagrams (FIG. 3A-3C) to illustrate examples of the cooperation and interaction between an SIMD and LIMD. FIGS. 3A-3C illustrate an SIMD timing diagram 302 and an LIMD timing diagram 350. The SIMD timing diagram 302 includes a cardiac signal sensing channel 304 and an event marker sensing channel 306. The cardiac signal sensing channel 304 receives a composite sensed cardiac signal 322, such as an intracardiac electrocardiogram, formed from cardiac signals sensed along one or more sensing vectors. The sensing vectors may be defined between various combinations of sensing electrodes available at the SIMD 14 (FIG. 1) (and/or lead 20). The event marker sensing channel 306 may be defined between the same combinations of sensing electrodes as used to sense cardiac signals. Optionally, the event marker sensing channel 306 may be defined between a different combination (or multiple different combinations) of the electrodes available at the SIMD 14 (FIG. 1) and lead 20. As explained above in connection with FIG. 2, in at least one embodiment, the cardiac signal and event marker sensing channels 304 and 306 utilize common electrodes, but separate sensing amplifiers and amplitude discriminators.

T-Wave Over-Sensing by the SIMD

As noted above, when operated alone, the SIMD may exhibit a potential to over-sense T-waves causing double counting of ventricular events. When T waves are over sensed, causing double counting of ventricular events, the SIMD may provide an inappropriate therapy. To avoid over sensing of T-waves, the LIMD provides R-wave verification. T-wave over sensing may otherwise occur as the SIMD may simply use threshold discrimination to identify R-waves. However, in some instances, the T-wave may also exhibit an amplitude that exceeds a threshold set for R-waves. Optionally, the threshold discrimination may use other morphology criteria that, at times, may be satisfied by R-waves and T-waves.

FIG. 3A is discussed hereafter in connection with avoiding oversensing, at the SIMD, of events that occur in the chamber where the LIMD is implanted, such as T-waves. In accordance with embodiments herein, the LIMD affords a very robust detector of events of interest that occur in the local chamber in which the LIMD is implanted. For example, when implanted in a ventricle, the LIMD provides a reliable R-wave detector. Based on the R-wave detection at the LIMD, communication between the LIMD and SIMD enable the SIMD to avoid T-wave over-sensing.

The LIMD timing diagram 350 illustrates a cardiac signal sensing channel 354 and therapy/marker channel 356. The cardiac signal sensing channel 354 illustrates a cardiac signal as sensed in the ventricle between one or more combinations electrodes on the LIMD. The channel 354 of the LIMD is tuned to listen in the near field for local events of interest (e.g., ventricular events) and does not notably detect remote activity (e.g., atrial event activity) for a remote chamber that differs from local chamber in which the LIMD is implanted. The LIMD analyzes the cardiac signals sensed over the channel 354 to identify intrinsic local events of interest (e.g. R-waves). When an intrinsic local event of interest is sensed, the LIMD delivers, over the therapy/marker channel 356, a near field (NF) event marker 360 that is temporally aligned/contemporaneous with a select point in the cardiac signal 322, such as the peak of the R-wave 325. When no intrinsic local event of interest is sensed before expiration of a corresponding timer, the LIMD delivers a pacing pulse. The LIMD may also generate the NF event marker 360 separate from, or as part, of a pacing pulse.

In various embodiments, the LIMD sends near field event markers to the SIMD when the LIMD detects an intrinsic R-wave or delivers a paced ventricular pulse. The NF event markers 360 are detected at 318 by the SIMD over a dedicated event marker sensing channel 306. For example, the event marker sensing channel 306 may be configured to reject lower frequency EGM signals (less than 500 hertz), but detect pacing pulses having frequency components in excess of 1 KHz. Alternatively, the LIMD may emit, as the event marker 360, very narrow high frequency pulses (on the order of several microseconds) to signal the SIMD that an R-wave or V-pace has taken place. The detected signal at 318 may be used by the SIMD to set up R-wave detection verification. For example, if the LIMD signals R-wave detection at ½ the rate that the SIMD detects R-waves, the SIMD is counting T-waves and R-waves, both as potential R-waves. As explained herein, the SIMD validates, from the potential R-waves, only R-waves that correspond with the detected signals at 318. The operations by the LIMD and SIMD to avoid over sensing are discussed below in connection with FIG. 4.

As another example, it may be desirable for the SIMD to track the T-waves as the event of interest. For example, certain behavior of T-waves, such as T-wave alternans, changes in ST-segment width, shift in ST-segment amplitude, T-wave amplitude, and the like, may be indicators of various heart conditions. Therefore, it may be desirable to correctly identify the T-wave, ST segment, etc., and avoid declaring other features of the cardiac signal as a T-wave.

P-Wave and R-Wave Sensing

Next, FIG. 3B is discussed in connection with enabling sensing of events of interest that occur in a remote chamber that differs from the local chamber in which the LIMD is implanted. For example, in accordance with at least one embodiment, methods and systems are provided that afford reliable P-wave tracking by an LIMD. An LIMD that is implanted in a ventricle is generally not well suited to sense atrial activity in the far field, and an LIMD implanted in an atrium may not adequately sense atrial activity in the far field. However, it may be desirable for an LIMD to track events of interest in a remote chamber such as P-waves for a ventricular LIMD or R-waves/T-waves for an atrial LIMD. In accordance with embodiments herein, the SIMD is configured to sense cardiac activity and identify remote (or far field) events of interest that occur in a chamber that is remote from the LIMD. The remote events of interest are remote relative to the LIMD. With the foregoing examples, the SIMD may, among other things, identify P-waves (as one example of an event of interest). The SIMD then informs the LIMD of the occurrence of the remote event of interest through generation of one or more far field (FF) event markers.

The timing diagram of FIG. 3B illustrates coordinated operation between an LIMD 16 and SIMD 14 where the LIMD 16 maintains various timers in connection with operation. In FIG. 3B, the LIMD 16 maintains an atrial alert period timer 382, an AV interval timer 384, a ventricular alert timer 386, a post ventricular atrial refractory period (PVARP) timer 388, a ventricular refractory period (Vref) timer 390, and MTRI timer 392 and a lower rate interval timer 394.

The SIMD timing diagram 302 includes a cardiac signal sensing channel 304, FF event marker sensing channel 306 and therapy/marker delivery channel 308. It is recognized that the sensing channel 306 may sense other features of interest in addition to the FF event markers. However, in connection with the present embodiment, the FF event marker is the item of interest to be sensed over the sensing channel 306. The cardiac signal sensing channel 304 senses a cardiac signal 322 that, in the example of FIG. 3B, includes an intrinsic P-wave 323. The SIMD monitors the sensing channel 304 and analyzes the cardiac signal 322 to identify events of interest that are remote to the LIMD, such as intrinsic P waves 323 (generally referred to as remote EOI). When an intrinsic P-wave 323 or other remote EOI is detected, the SIMD delivers a P-wave trigger or FF event marker 309 over the therapy/marker delivery channel 308.

The SIMD performs far field sensing by capturing the high-resolution cardiac signal 322 similar to a surface ECG. The SIMD analyzes the cardiac signal 322 to identify an atrial event within the composite electrogram cardiac signal 322 that is received on the channel 304 associated with programmed sensing vector(s). The composite electrogram cardiac signal 322 provides a PQRS signal morphology from which an atrial portion (associated with a P-wave) may be extracted based on various signal analysis methods.

A desired sensing configuration can be selected by the clinician or by an automatic algorithm. For example, the clinician or an automated algorithm may set one or more sensing thresholds (e.g. a P-wave threshold) and timing intervals/windows. During the chosen timing window(s), the SIMD monitors the cardiac signal and identifies peaks in the cardiac signal that exceed the P-wave sensing threshold. When the SIMD detects an atrial event that exceeds the P-wave sense threshold within the P-wave timing window, the SIMD declares an atrial event to occur. Additionally or alternatively, other thresholds may be utilized to detect other remote EOI (e.g., the ST segment length, ST segment amplitude, etc.).

The LIMD timing diagram 350 illustrates a cardiac signal sensing channel 354, an event marker sensing channel 352 and a therapy/marker delivery channel 356. The LIMD detects the FF (atrial) event marker at 311 over the event marker sensing channel 352. Upon detection of an FF event marker at 311, the LIMD initiates the AV interval timer 384 and monitors the cardiac sensing channel 354 for an intrinsic ventricular event. When an intrinsic ventricular event does not occur before the AV interval timer 384 times out, the LIMD delivers a pacing pulse 357 over the delivery channel 356. Within the sensing channels 304 and 306, blanking intervals 324 and 326 are denoted. During the blanking intervals 324 and 326 the sensing channels 304 and 306 are rendered insensitive. The pacing pulse 357 initiates a paced ventricular event 353 which is sensed at the SIMD at 322.

The second pacing pulse 357 includes an event marker that is sensed at the SIMD over the event marker sensing channel 306, such as denoted at 359 (corresponding to the dashed linking line 361).

In accordance with embodiments herein, P-wave detection by the SIMD may be facilitated with information by the LIMD. For example, the SIMD utilizes a timing window to determine when to listen for P-waves. The timing of the window is based on an R-wave detected by the SIMD. As explained herein, the SIMD may mischaracterize candidate events in the cardiac signal as an event of interest (e.g., mischaracterize T-waves as R-waves). The SIMD utilizes event markers received from the LIMD to validate the events of interest, such as to correctly identify an R-wave. Once the SIMD validates an event of interest (R-wave), the SIMD sets the subsequent timing window to listen for the next P-wave based on the R-wave as validated by the event marker from the LIMD.

Optionally, the event marker may be presented as a non-pacing pulse as explained herein. The SIMD detects the event marker in the pacing pulse 357, as noted at 359 and initiates one or more related timing intervals such as a post ventricular atrial refractory period (PVARP), a maximum tracking rate interval (MTRI), an atrial alert period and the like. When P-waves are detected before expiration of the MTRI, the P-wave is treated as occurring at the end of the MTRI. The LIMD communicates the event markers to the SIMD in various manners. For example, upon detection of an R-wave, the LIMD triggers a V-pace that is detected by the SIMD as a ventricular event. In an alternate embodiment, the LIMD may signal the SIMD by emitting very narrow high frequency pulses that are detected by the SIMD to signify that an R-wave or a V-pace has occurred using a special amplifier known as the SIMD pulse amp. The SIMD incorporates a high frequency pulse detection circuit (e.g. within the sensing circuits 32, 34) that rejects electrograms having frequencies less than 500 hertz but passes narrow pulses. Additionally or alternatively, within the sensing circuit 32, 34, an amplifier may be utilized that has adequate mid frequency response in the 2 to 10 KHz range in order to detect both V-pace pulses and high frequency pulses signal pulses.

Additionally or alternatively, a processor within the SIMD may perform a filter matching operation that is configured to detect P-waves by correlating the composite electrogram incoming cardiac signals 322 with a P-wave template. For example, the SIMD may perform correlation using an abbreviated correlator.

The SIMD and LIMD use separate sensing thresholds for the atrial signal and the ventricular signal controlled by the atrial and ventricular refractory period timing. Additionally or alternatively, the SIMD and LIMD may transmit one or both of a P-wave marker and an R-wave marker to one another. The sensing electrode configurations can be dynamically changed within a cardiac cycle to facilitate discrimination between P and R-waves.

SIMD Triggered Pacing

Next, FIG. 3C is discussed in connection with utilizing the SIMD 14 to trigger therapy by the LIMD 16. The timing diagram of FIG. 3C shows the coordination between a LIMD 16 and SIMD 14 operating jointly, where the LIMD 16 provides at least one type of therapy and the SIMD 16 provides at least one other type of therapy. The LIMD is set in a VDD mode with preprogrammed base rates. The SIMD timing diagram 302 includes SIMD composite cardiac signal sensing channel 304, SIMD marker sensing channel 306 and SIMD therapy delivery channel 308. The sensing channel 304 senses a P-wave 323 and an R-wave 325. Within the sensing channels 304 and 306, blanking intervals 324 and 326 are denoted. During the blanking intervals 324 and 326 the sensing channels 304 and 306 are rendered insensitive.

The SIMD manages various timing intervals, such as an AV interval timer 330, a post ventricular atrial refractory period (PVARP) timer 332 and maximum tracking rate interval 334 and an atrial alert period timer 336. The AV time delay 330 is initiated upon detection of an intrinsic P-wave 323. When the AV time delay 330 times out, the SIMD delivers a ventricular trigger event marker 328 representing an instruction to the LIMD to deliver a pacing pulse in the ventricle. The ventricular trigger event marker 328 is detected at 340 over an LIMD marker sensing channel 352. In response thereto, the LIMD delivers a ventricular pacing pulse at 342 over the therapy channel 356.

The LIMD manages various timing intervals, such as a ventricular refractory timer 364, a ventricular alert period timer 366, a lower rate interval 368 and the like. Once the LIMD delivers a pacing pulse 342, the ventricular refractory interval 364 is set, followed by the ventricular alert period 366. The ventricular refractory (Vref) interval 364 represents a time period during which the ventricle is expected to remain in a refractory state. Upon conclusion of the Vref interval 364, a ventricular alert period 366 is started. During the ventricular alert period 366, an intrinsic ventricular event is not expected. When an intrinsic ventricular event occurs during a ventricular alert period 366, certain corrective actions may be taken. The SIMD generates a ventricular trigger pulse 328 over the therapy/marker delivery channel 308. If an intrinsic ventricular event or ventricular trigger pulse 328 is not detected by the end of the ventricular alert period 366, the LIMD delivers a pacing pulse 370. The SIMD detects the pacing pulse at 372 and in response thereto initiates the PVARP timer 332.

The timers and intervals may represent state machines, firmware or software based timers utilized by the LIMD and SIMD. Optionally, the timers and intervals may be varied in duration, be omitted entirely or additional timing intervals may be added.

Links 378, 380 are denoted in dashed lines to indicate that the triggering pulses 328 and pacing pulse 370 are sensed by the other one of the LIMD and SIMD. As explained herein, the delivery and sensing of event markers at select times enables communication and coordinated operation between the LIMD and SIMD. The event markers have a predetermined pattern that is configured to indicate that an event of interest has occurred in a corresponding chamber of the heart in which the atrial or ventricular LIMD is located. Based upon the time at which an event marker is delivered, as well as the device (atrial or ventricular) from which the event marker is produced, such event markers will have different meanings and cause the initiation of a related action from the other device.

Alternatively or additionally, the LIMD and SIMD may coordinate operation when switching modes of operation. For example, the LIMD controller may analyze the cardiac signal for noise reversion and enter an asynchronous pacing mode when detecting the noise reversion. When the LIMD enters the noise reversion mode, the LIMD controller generates a mode switching pulse that is delivered over the therapy/marker delivery channel. The SIMD detects the mode switching pulse over the pulse sensing channel and the SIMD controller recognizes the mode switching pulse to indicate that the LIMD is entering the asynchronous pacing mode. The SIMD may continue to operate in the same manner as before detecting the mode switching pulse, or alternatively, the SIMD may change/perform one or more operations based on detection of the mode switching pulse.

Figure 4:
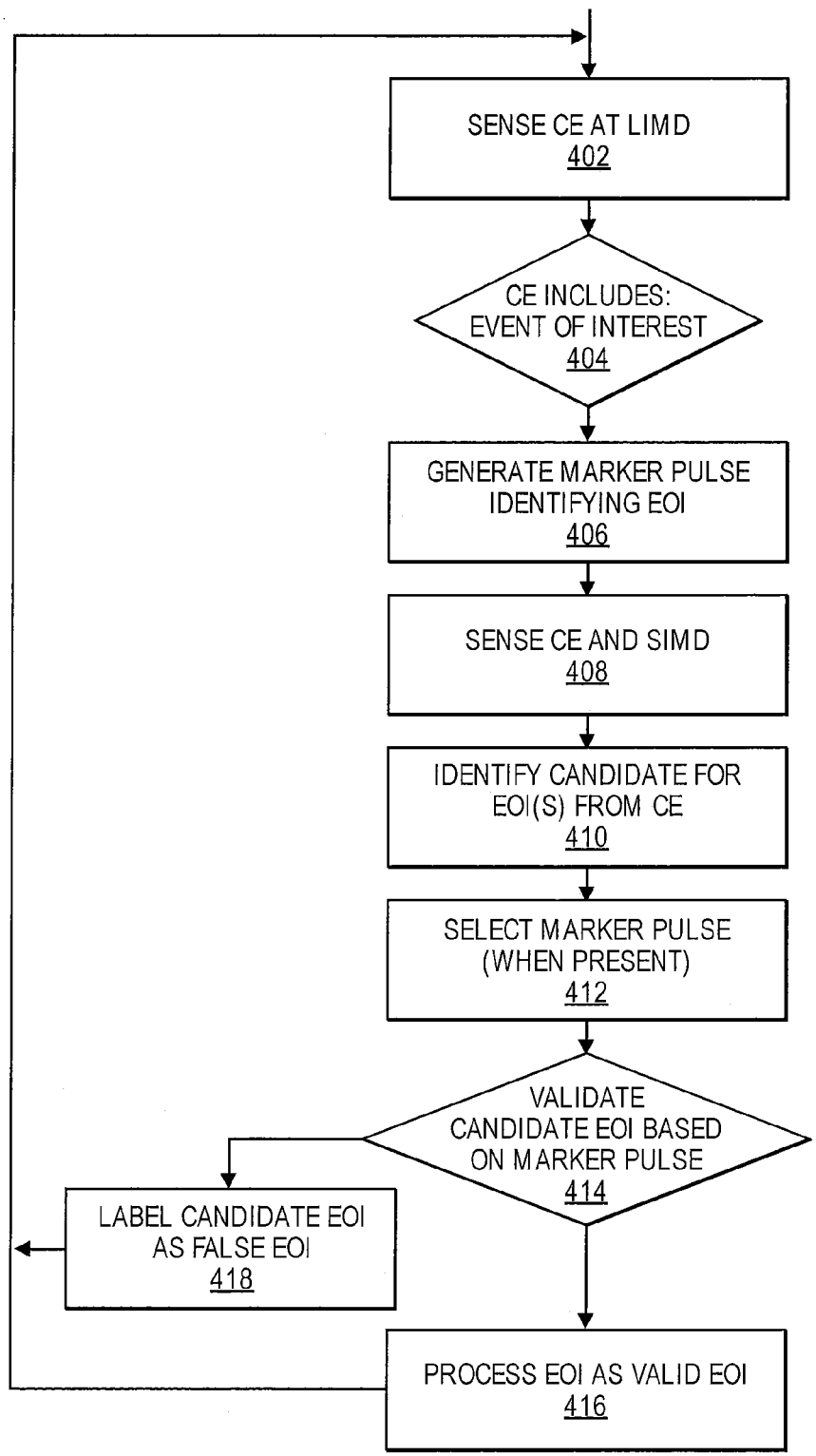
FIG. 4 illustrates a method to prevent over counting (or over sensing) events of interest in accordance with an embodiment herein based on communication of marker pulses between the SIMD and LIMD in accordance with an embodiment herein.

FIG. 4 illustrates a method to prevent over counting (or over sensing) events of interest in accordance with an embodiment herein based on communication of event markers between the SIMD and LIMD. It should be recognized, that while the operations of FIG. 4 are described in a somewhat serial manner, one or more of the operations of FIG. 4 are performed continuously and in parallel with one another. For example, the various operations performed by the LIMD may be continuous and performed in parallel with the operations performed by the SIMD, and vice versa.

The LIMD and SIMD are configured to be implanted, where the LIMD is implanted entirely within a first local chamber of the heart. The LIMD is configured to deliver at least one type of therapy (e.g. a pacing therapy) within the local chamber. The SIMD is configured to be implanted proximate to the heart, but outside of the heart. The SIMD is configured to deliver at least one other type of therapy (e.g. a ventricular tachycardia (VT), defibrillation or other arrhythmia therapy). The LIMD and SIMD may deliver similar types of therapy (e.g. antitachycardia pacing), however the SIMD may be able to provide additional therapy options not available on the LIMD due to size, power constraints, electrode positions and the like. Beginning at 402, the LIMD begins sensing cardiac signals representative of one or more intrinsic and/or paced cardiac events (CE). The types of cardiac events sensed is dependent upon which local chamber the LIMD is implanted. The first chamber is also referred to as the local chamber in which the LIMD implanted.

At 404, the sensed cardiac signals are analyzed at the LIMD for a local event of interest (EOI) occurring in the local chamber.

At 406, based on the analysis, a near field (NF) event marker is produced from an electrode or electrodes of the LIMD when an event of interest occurs in the first or local chamber.

At 408, the SIMD senses cardiac signals representative of one or more cardiac events (CE) along one or more sensing vectors that are defined by the electrodes 22, 24, and the housing 18. The cardiac signals sensed by the SIMD may include one or more intrinsic or paced events.

At 410, the SIMD analyzes the sensed cardiac signals to identify candidate events of interest (EOI) associated with cardiac events. For example, the event of interest may represent the peak of the R-wave, the peak of a T-wave, and the like.

At 412, the SIMD detects NF event markers transmitted from the LIMD. As explained herein, the event markers are transmitted by the LIMD temporally contemporaneous with occurrence of one or more events of interest detected by the LIMD. For example, when the event of interest corresponds to the peak of the R-wave, the LIMD transmits an event marker each time the LIMD detects an R-wave peak. Consequently, at 412, the SIMD receives an event marker each time the LIMD detects an R-wave peak.

At 414, the SIMD determines whether to validate one or more candidate events of interest (namely to declare the candidate EOI valid or invalid). The validation determination is made based, at least in part, upon detection of one or more NF event markers. For example, when the SIMD determines that an NF event marker was detected temporally contemporaneous in time with detection of an event of interest at the SIMD, the corresponding event of interest is declared to represent a valid event of interest. Alternatively, when a candidate event of interest occurs in time without a corresponding temporally contemporaneous NF event marker, the SIMD declares the candidate event of interest to represent an invalid or false EOI.

At 416, the SIMD processes each valid EOI. For example, when valid EOI's corresponds to the peaks of the R-wave, the SIMD may monitor the R-wave peaks in connection with determining whether the heart rate falls within or exceeds various program thresholds. When the heart rate (as defined by valid R-wave peaks) exceeds an upper threshold, the SIMD may deliver a corresponding therapy, such as a defibrillation shock, a cardioversion therapy, antitachycardia pacing therapy and the like. Thereafter, flow returns to 402.

At 418, the SIMD labels the candidate EOI as a false EOI and flow returns to 402. The operations of FIG. 4 are iteratively repeated throughout use of the LIMD and SIMD to provide appropriate therapies. For example, the LIMD may provide pacing and/or antitachycardia pacing therapy continuously over time while sensing cardiac signals representative of cardiac events, and generating event markers identifying an event of interest. The SIMD may provide pacing, cardioversion, ATP, defibrillation or other therapies continuously over time while sensing cardiac signals representative of cardiac events and monitoring for event markers used to validate candidate EOIs.

Optionally, the SIMD may automatically adjust at least one of a sensing vector, sensing threshold and AV refractory interval based on a number of the candidate EOIs that are declared to be invalid EOIs due to a lack of corresponding event markers. For example, when the SIMD detects an excess plurality of the event markers within a predetermined period of time, the SIMD may enter a marker-disable mode and disregard the event markers when declaring candidate EOIs as valid or invalid EOIs. Accordingly, the operations of FIG. 4 avoid over sensing an event of interest by the SIMD. As examples, the over sensed event may represent R-waves, T-waves, ST-segments and the like.

Figure 5:
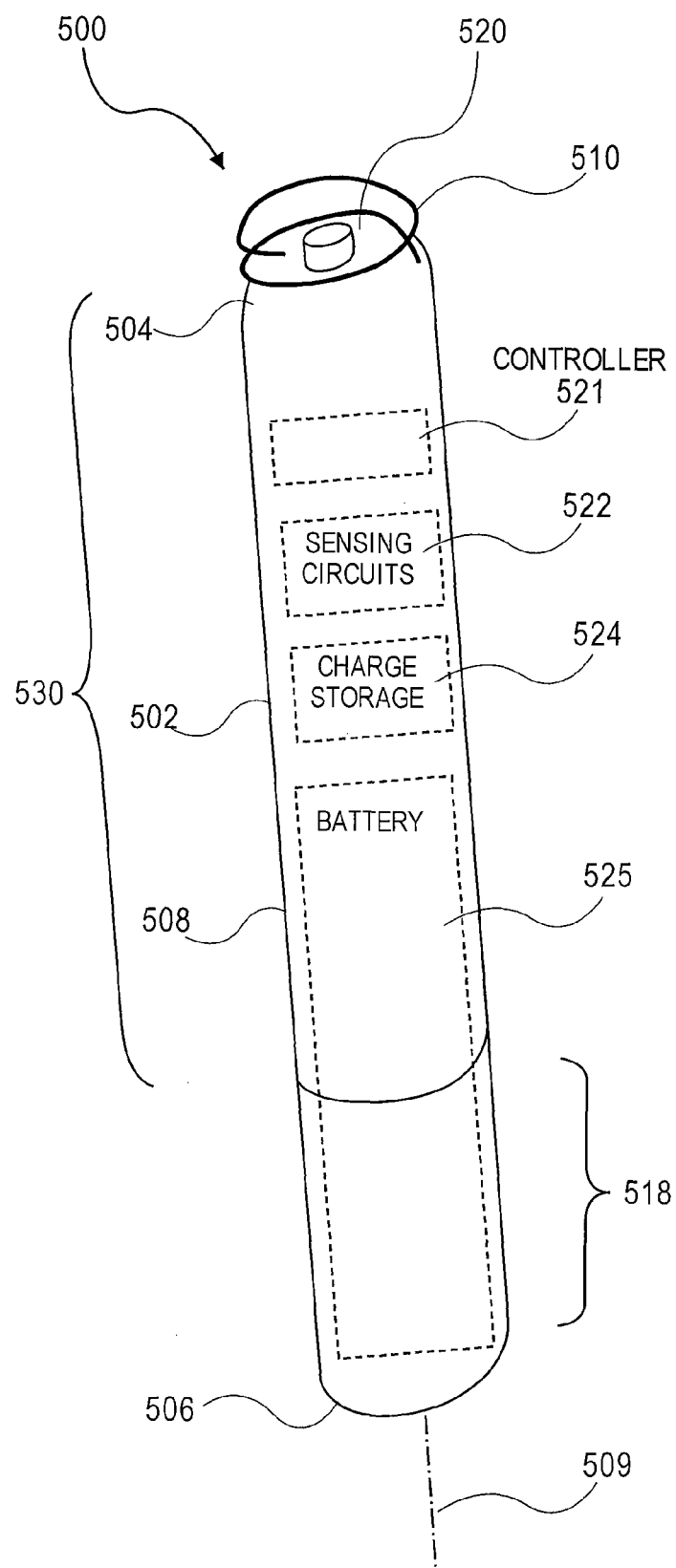
FIG. 5 illustrates an LIMD formed in accordance with an embodiment herein.

FIG. 5 illustrates an LIMD 500 in accordance with an embodiment herein. The LIMD 500 comprises a housing 502 having a distal end 504, a proximal end 506, and an intermediate shell 508 extending between the distal end 504 and the proximal end 506. The shell 508 is elongated and tubular in shape and extends along a longitudinal axis 509. The LIMD 500 includes a battery 525 for power supply.

The distal end 504 includes one or more electrodes 520 securely affixed thereto and projected outward. A fixation mechanism 510 may be wound around electrode 520. In certain embodiments, fixation mechanism 510 may be formed as large semi-circular spikes or large gauge wires that wrap only partially about the inner electrode 520. Fixation mechanism 510 may be used exclusively for fixation of the pacer to the tissue. In this case it would be inactive electrically and may be coated with an insulator like parylene or may be simply not connected to the case or any associated circuitry. Alternatively, fixation mechanism 510 may also be used as an electrode to detect the local potentials from the tissue surrounding the electrode 520 and fixation mechanism 510. In other embodiments, a second electrode located on the distal end 504 but not included on fixation mechanism 510, may be used to sense between the second electrode and electrode 520 to detect the local potentials from the surrounding tissues.

This allows for exclusive detection of electrograms from the local tissue (in the same chamber as the LIMD 500) such that only ventricular activity is detected by a ventricle LIMD and atrial activity is exclusively detected by an atrium LIMD. This selective sensing is useful for excluding ventricular depolarization in the atrium. Avoiding sensing of far field R-waves at an atrial LIMD enables atrial event tracking and sensing of atrial arrhythmias with little or no confounding of atrial sensing due to far field R-waves. When the atrial LIMD is "desensitized" to ventricular far field signals, the timing of the atrial LIMD may be updated to set the PVAB to be very short.

Conversely sensing between fixation mechanism 510 configured to include an electrode and electrode 520 in the ventricle excludes any sensing of atrial activity in the ventricle even if the ventricular LIMD is located in tissue proximate to the atrium, like the right ventricular septum or vestibule of the RV. This prevents inappropriate detection by the ventricular LIMD of atrial depolarizations as ventricular events, which might otherwise detract from the processes described herein.

Included at the proximal end 506 of the LIMD is an electrode 518. Electrode 518 is electrically connected to the sensing circuits 522 and is used to perform pulse sensing. The pulse sensing is performed between electrode 520, the stimulation cathode, and electrode 518, the anode. Because the cathode electrode 520 and anode electrode 518 are relatively widely separated, it makes it possible for the LIMD to communicate using the event markers and pacing pulses at relatively large distances. This is true for communication from the ventricle to the atrium as well as communication from the atrium to the ventricle. In between cathode electrode 520 and anode electrode 518 is an insulated region 530 that separates the pulse sensing electrodes 520 and 518. The region 530 may be insulated with a parylene coating.

Pulses are generated by the charge storage circuit 524 and are emitted between cathode electrode 520 and anode electrode 518 for both stimulation and communication between the devices. Because of the relatively large separation between these electrodes 518 and 520, the dipole field generated in the tissue is large as well and this also facilitates communication using pacing pulses and triggered pulses between the devices. So the relatively large separation between the electrodes 520 and 518 facilitates both reception and transmission of the information carried on the pulses over relative large distances in the body. For example, the distance between electrodes 520 and 518 may be one-half to two-thirds of the overall length of the LIMD 500 (e.g., over 5 mm, 5-20 mm, up to 30 mm).

If fixation mechanism 510 is electrically active, it may also be used for sensing pulses using the sensing circuits 522 and in addition it may be used for providing triggered pulses. In addition if pacing is performed between the electrode of fixation mechanism 510 and electrode 520, then communication between the chambers using the pacing pulses is avoided because the local dipole is so small that there is little or no signaling to the remote LIMD doing sensing. This is useful if the atrial LIMD performs atrial tachycardia pacing.

The LIMD 500 includes a charge storage unit 524 and sensing circuit 522 (including cardiac event sensing circuitry 32 and pulse sensing circuitry 34 shown in FIG. 2) within the housing 502. The sensing circuit 522 senses intrinsic activity, while the charge storage unit 524 stores high or low energy amounts to be delivered in one or more stimulus pulses. The sensing circuit 522 senses intrinsic and paced events, as well as event markers. The electrode of fixation mechanism 510 and electrode 520 may be used to deliver lower energy or high energy stimulus, such as pacing pulses, cardioverter pulse trains, and the like. The electrodes 520, 518 also sense event markers as described herein. The electrodes 520, 518 may also be used to sense electrical activity, such as physiologic and pathologic behavior and events and provide sensed signals to the sensing circuit 522.

The electrodes 520, 518 are configured to be joined to an energy source, such as a charge storage unit 524. The electrodes 520, 518 receive stimulus pulse(s) from the charge storage unit 524. The electrodes 520, 518 are configured to deliver high or low energy stimulus pulses to the myocardium.

The LIMD 500 includes a controller 521, within the housing 502 to cause the charge storage unit 524 to deliver activation pulses through each of the electrodes 520, 518 in a synchronous manner, based on information from the sensing circuit 522, such that activation pulses delivered from the inner electrode 520 are timed to initiate activation in the adjacent chamber. The controller 521 performs the various operations described herein in connection with embodiments for the systems and the methods. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. Among other things, the LIMD controller 521 is configured to analyze the cardiac signals and, based thereon, to produce a near field event marker indicative of a local event of interest occurring in the local chamber. The LIMD controller 521 generates the NF event marker contemporaneous in time with the local event of interest. For example, the local event of interest may represent an R-wave or a T-wave (e.g., when implanted in the ventricle) or a P-wave (e.g., when implanted in the atrium). The LIMD controller 521 may produce, as the NF event marker, at least one of a pacing pulse and a communications pulse. Optionally, the LIMD controller 521 may analyze the cardiac signal for noise reversion and enter an asynchronous pacing mode when detecting the noise reversion. The LIMD controller 521 generates a mode switching pulse and the SIMD controller recognizes the mode switching pulse to indicate that the LIMD is entering the asynchronous pacing mode. The LIMD controller 521 is also configured to initiate an interval timer based on detection of FF event markers (from the SIMD) and based thereon, to delivery a pacing pulse. For example, the LIMD controller 521 analyzes the cardiac signal for an intrinsic near field (NF) event, and delivers the pacing pulse when the intrinsic NF event is not present in the cardiac signal before the interval timer times out. The LIMD controller 521 may also be configured to analyze the cardiac signals and, based thereon, produce a near field event marker when a local EOI occurs in the local chamber. The SIMD controller is configured to set a P-wave timing window based on receipt of the NF event marker, the SIMD controller searching for an atrial event during the P-wave timing window.

Figure 6:
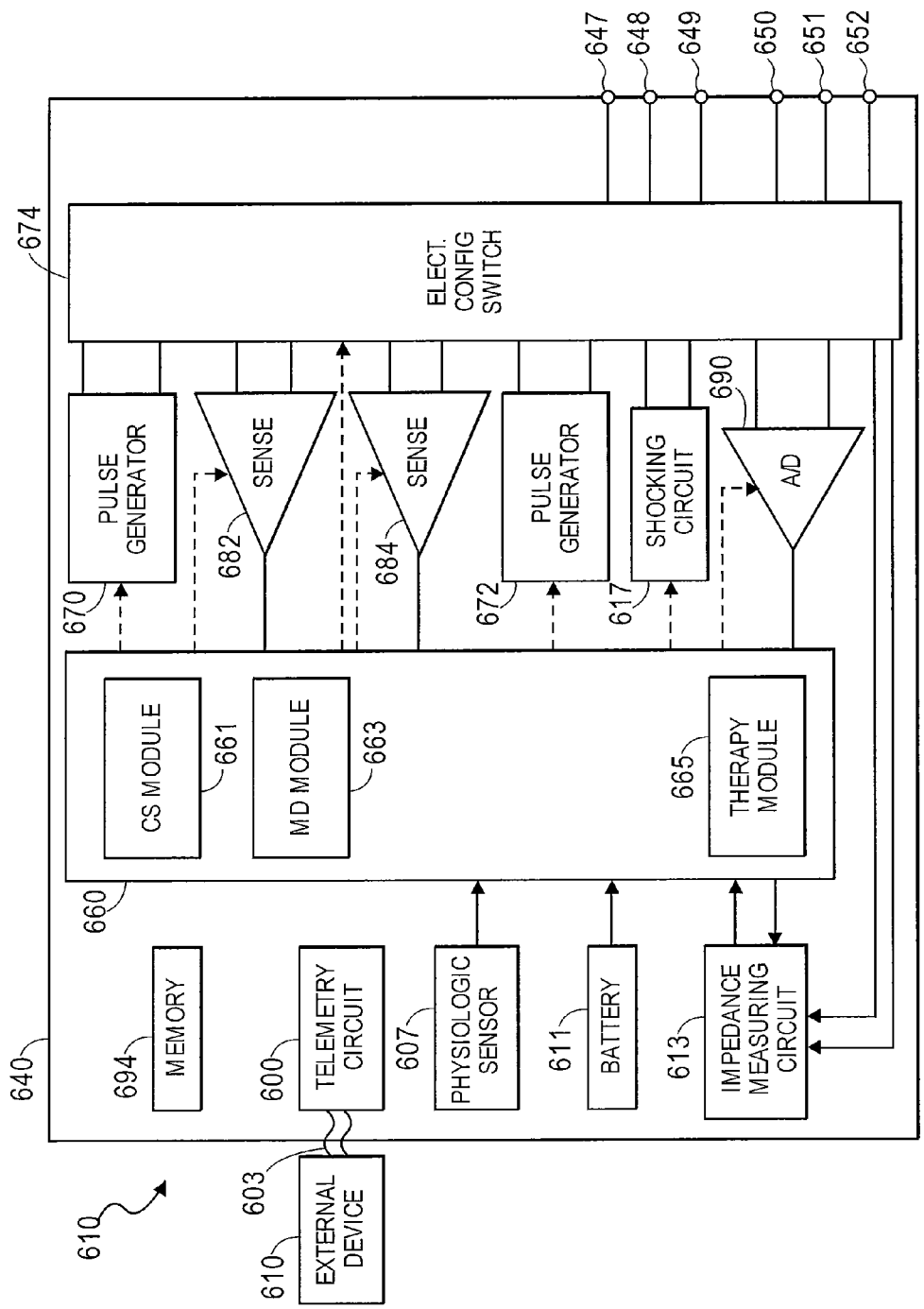
FIG. 6 illustrates a block diagram of an LIMD and/or SIMD, which is capable of performing the methods described herein and of treating one or both of fast and slow arrhythmias with stimulation therapy, including cardioversion, defibrillation, and pacing stimulation.

FIG. 6 illustrates a block diagram of an LIMD and/or SIMD 610 (hereafter collectively the device 610), which is capable of performing the methods described herein and of treating one or both of fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

The housing 640 for the stimulation device 610 is often referred to as the "can", "case" or "case electrode" and may be programmably selected to act as the return electrode for some or all sensing modes. The housing 640 may further be used as a return electrode alone or in combination with one or more other electrodes. The housing 640 further includes a connector (not shown) having a plurality of terminals 647-652. To achieve sensing, pacing and shocking in connection with desired chambers of the heart, the terminals 647-652 are selectively connected to corresponding combinations of electrodes.

The device 610 includes a programmable microcontroller 660 that controls the various modes of sensing and stimulation therapy. The microcontroller 660 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 660 includes the ability to process or monitor input signals (data) as controlled by a program code stored in memory. The details of the design and operation of the microcontroller 660 are not critical to the present invention. Rather, any suitable microcontroller 660 may be used. The microcontroller 660 performs the operations describe herein in connection with FIGS. 3A-3C, 4 and elsewhere.

The microcontroller 660 includes inputs that are configured to collect cardiac signals associated with electrical or mechanical behavior of a heart over at least one cardiac cycle. The cardiac signals may be IEGM signals from the cardiac sensing circuit 682 representative of electrical behavior of the heart. The circuit 682 may provide separate, combined, composite or difference signals to the microcontroller 660 representative of the sensed signals from the electrodes. Optionally, the cardiac signals may be the output of the A/D circuit 690 that are representative of electrical behavior of the heart. The cardiac signals may be the output of the physiologic sensor 607 that are representative of mechanical behavior.

The microcontroller 660 includes a cardiac signal (CS) module 661, a marker detection (MD) module 663 and a therapy module 665 (among other things). The CS module 661 is configured to analyze cardiac signals as discussed herein. The MD module 663 is configured to analyze signals sensed over the marker sensing channel and identify incoming event markers. The therapy module 665 is configured to modulate, over multiple cardiac cycles, at least one therapy parameter while the device 610 obtains a collection of at least one CSF indicators associated with different therapy parameters. The therapy module 665 is further configured to adjust a therapy configuration based on, among other things, the cardiac signals and based on the event markers.

The microcontroller 660 further controls a shocking circuit 617 by way of a control signal. The shocking circuit 617 generates stimulating pulses of low (up to 0.5 Joules), moderate (0.5-10 Joules), or high energy (11 to 40 Joules), as controlled by the microcontroller 660. Stimulating pulses are applied to the patient's heart through at least two shocking electrodes.

One or more pulse generators 670 and 672 generate various types of therapy, such as pacing and ATP stimulation pulses for delivery by desired electrodes. The electrode configuration switch 674 (also referred to as a switch bank) controls which terminals 647-652 are connected to the pulse generators 670, 672, thereby controlling which electrodes receive a therapy. The pulse generators, 670 and 672, may include dedicated, independent pulse generators, multiplexed pulse generators, shared pulse generators or a single common pulse generator. The pulse generators 670 and 672 are controlled by the microcontroller 660 via appropriate control signals to trigger or inhibit stimulation pulses. The microcontroller 660 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 674 connects the sensing electronics to the desired terminals 647-652 of corresponding sensing electrodes. For example, a portion of the terminals may be coupled to electrodes configured to define a sensing and/or shocking vector that passes through the left ventricle. The switch 674 may connect terminals to the event marker sensing circuit 684 (which corresponds to the event marker sensing channel) and the microcontroller. The circuit 684 may amplify, filter, digitize and/or otherwise process the sensed signals from the select electrodes.

The switch 674 also connects various combinations of the electrodes to an impedance measurement circuit 613. The impedance measuring circuit 613 includes inputs to collect multiple measured impedances between corresponding multiple combinations of electrodes. For example, the impedance measuring circuit 613 may collect a measured impedance for each or a subset of the active sensing vectors. Optionally, the impedance measuring circuit 613 may measure respiration or minute ventilation; measure thoracic impedance for determining shock thresholds; detects when the device has been implanted; measures stroke volume; and detect the opening of heart valves, etc.

The switch bank 674 includes a plurality of switches for connecting the desired electrodes to the appropriate I/O circuits, thereby providing complete electrode programmability. The switch 674, in response to a control signal from the microcontroller 660, determines the polarity of the stimulation pulses (e.g., unipolar, bipolar, co-bipolar, etc.) by selectively closing the appropriate combination of switches (not specifically shown). The outputs of the cardiac signal and event marker sensing circuits 682 and 684 are connected to the microcontroller 660 which, in turn, is able to trigger or inhibit the pulse generators 670 and 672, respectively. The sensing circuits 682 and 684, in turn, receive control signals from the microcontroller 660 for purposes of controlling the gain, threshold, the polarization charge removal circuitry (not shown), and the timing of any blocking circuitry (not shown).

Cardiac signals are also applied to the inputs of an analog-to-digital (ND) data acquisition system 690. The data acquisition system 690 is configured to acquire intracardiac electrogram signals, convert the raw analog data into a digital signal, and store the digital signals for later processing and/or telemetric transmission to an external device 610. The data acquisition system 690 samples cardiac signals across any pair of desired electrodes. The data acquisition system 690 may be coupled to the microcontroller 660, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 660 is further coupled to a memory 694 by a suitable data/address bus 696. The memory 694 stores programmable operating, impedance measurements, impedance derivation and therapy-related parameters used by the microcontroller 660. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 694 through a telemetry circuit 600 in telemetric communication with the external device 610, such as a programmer, trans-telephonic transceiver, or a diagnostic system analyzer. The telemetry circuit 600 is activated by the microcontroller 660 by a control signal. The telemetry circuit 600 advantageously allows intracardiac electrograms and status information relating to the operation of the device (as contained in the microcontroller 660 or memory 694) to be sent to an external device 610 through an established communication link 603.

The stimulation device 610 may include a physiologic sensor 607 to adjust pacing stimulation rate according to the exercise state of the patient. The physiological sensor 607 may further be used to detect changes in cardiac output, changes in the physiological condition of the heart, or diurnal changes in activity (e.g., detecting sleep and wake states). The battery 611 provides operating power to all of the circuits shown in FIG. 6.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

What is claimed is:

1. A distributed implantable system, comprising:
a leadless implantable medical device (LIMD) configured to be implanted entirely within the heart and to deliver a pacing therapy, the LIMD comprising:
a housing having a proximal end configured to engage local tissue of interest in a local chamber;
electrodes located along the housing;
LIMD cardiac sensing circuitry to sense cardiac signals; and
a LIMD controller configured to analyze the cardiac signals and, based thereon, to produce a near field (NF) event marker indicative of a local event of interest (EOI) occurring in the local chamber; and
a subcutaneous implantable medical device (SIMD) to be located proximate to the heart and configured to deliver an arrhythmia therapy, the SIMD comprising:
SIMD cardiac sensing circuitry to sense cardiac signals;
a SIMD controller configured to identify a candidate EOI from the cardiac signals;
pulse sensing circuitry to detect the NF event marker from the LIMD; and
the SIMD controller configured to declare the candidate EOI as a valid EOI or an invalid EOI based on the NF event marker.

2. The system of claim 1, wherein the SIMD controller is configured to track valid EOIs based on NF event markers to avoid over sensing candidate EOIs.

3. The system of claim 1, wherein the event of interest corresponds to an R-wave of the cardiac signal, the SIMD controller identifying both an R-wave and a T-wave from the cardiac signals as candidate events of interest, the SIMD controller declaring the R-wave as the valid event of interest and the T-wave as the invalid event of interest based on the NF event marker.

4. The system of claim 3, wherein the LIMD controller generates the NF event marker contemporaneous in time with the R-wave, representing the event of interest, the SIMD controller utilizing the NF event marker to avoid tracking the T-wave in the cardiac signal as another R-wave.

5. The system of claim 1, wherein the LIMD controller produces, as the NF event marker, at least one of a pacing pulse and a communications pulse.

6. The system of claim 1, the SIMD cardiac sensing circuitry further comprises a discriminator configured to only pass cardiac signals that exceed a select sensing threshold.

7. The system of claim 1, wherein the LIMD controller analyzes the cardiac signal for noise reversion and enters an asynchronous pacing mode when detecting the noise reversion, the LIMD controller generating a mode switching pulse, the SIMD controller recognizing the mode switching pulse to indicate that the LIMD is entering the asynchronous pacing mode.

8. The system of claim 1, wherein the SIMD automatically adjusts at least one of a sensing vector, sensing threshold and AV refractory interval based on a number of the candidate EOIs that are declared to be invalid EOIs due to a lack of corresponding NF event markers.

9. The system of claim 1, wherein, when the SIMD detects an excess plurality of the NF event markers within a predetermined period of time, the SIMD enters a marker-disable mode and disregards the NF event markers when declaring candidate EOIs as valid or invalid EOIs.

10. A distributed implantable system, comprising:
a leadless implantable medical device (LIMD) configured to be implanted entirely within a local chamber of the heart; and
a subcutaneous implantable medical device (SIMD) configured to deliver an arrhythmia therapy, the SIMD comprising:
SIMD cardiac sensing circuitry to sense cardiac signals; and
a SIMD controller configured to analyze the cardiac signals and based thereon, to produce a far field (FF) event marker indicative of a remote event of interest (EOI) occurring in a remote chamber that differs from the local chamber;
the LIMD comprising:
a housing having a proximal end configured to engage local tissue of interest in the local chamber;
electrodes located along the housing;
LIMD cardiac sensing circuitry to sense cardiac signals;
LIMD pulse sensing circuitry to detect the FF event marker; and
a LIMD controller configured to initiate an interval timer based on detection of the FF event marker and based thereon, to deliver a pacing pulse.

11. The system of claim 10, wherein the LIMD controller analyzes the cardiac signal for an intrinsic near field (NF) event, and delivers the pacing pulse when the intrinsic NF event is not present in the cardiac signal before the interval timer times out.

12. The system of claim 10, wherein the local chamber is a ventricle and the remote EOI represents a P-wave, the SIMD transmits the FF event marker to direct the LIMD to initiate a PV interval timer as the interval timer, the LIMD to deliver a ventricular pacing pulse when the LIMD is not inhibited by an intrinsic R-wave representing the intrinsic local event.

13. The system of claim 10, wherein the SIMD controller declares an atrial event to occur as the remote EOI in response to detecting an atrial event that exceeds a P-wave sense threshold within a P-wave timing window.

14. The system of claim 10, wherein the LIMD controller is configured to analyze the cardiac signals and, based thereon, produce a near field (NF) event marker when a local EOI occurs in the local chamber; and wherein the SIMD controller is configured to set a P-wave timing window based on receipt of the NF event marker, the SIMD controller searching for an atrial event during the P-wave timing window.

15. A method for coordinating operation of a distributed implantable system having a leadless implantable medical device (LIMD) to be implanted entirely within a local chamber of the heart and to deliver a pacing therapy and having a subcutaneous implantable medical device (SIMD) to be located proximate to the heart and to deliver an arrhythmia therapy, the method comprising:
programming the LIMD to sense and analyze cardiac signals and, based thereon, to produce a near field (NF) event marker indicative of a local event of interest (EOI) occurring in the local chamber;
configuring the SIMD to sense cardiac signals and to sense the NF event marker from the LIMD; and
programming the SIMD to identify a candidate EOI from the cardiac signals and to declare the candidate EOI as a valid EOI or an invalid EOI based on the NF event marker.

16. The method of claim 15, further comprising declaring, at the SIMD, the candidate EOI to be a valid EOI when the NF event marker is detected temporally contemporaneous with occurrence of the candidate EOI.

17. The method of claim 15, wherein the programming further comprises programming the SIMD controller to avoid over sensing candidate EOIs as valid EOIs by tracking valid EOIs based on the NF event markers.

18. The method of claim 15, wherein the local EOI corresponds to an R-wave, the method further comprising identifying both an R-wave and a T-wave from the cardiac signals as candidate EOIs, and declaring the R-wave as the valid EOI and the T-wave as the invalid EOI based on the NF event marker.

19. A method for coordinating operation of a distributed implantable system having a leadless implantable medical device (LIMD) to be implanted entirely within a local chamber of the heart to deliver a pacing therapy and having a subcutaneous implantable medical device (SIMD) to be located proximate to the heart and to deliver an arrhythmia therapy, the method comprising:
programming the SIMD to sense and analyze cardiac signals and, based thereon, to produce a far field (FF) event marker indicative of a remote event of interest (EOI) occurring in a remote chamber different from the local chamber;
configuring the LIMD to sense cardiac signals and to sense the FF event marker from the SIMD; and
initiating an interval timer, at the LIMD, based on detection of the FF event marker; and
configuring the LIMD to deliver a pacing pulse based on the interval timer.

20. The method of claim 19, further comprising analyzing the cardiac signals sensed by the LIMD for an intrinsic near field (NF) event, and delivering the pacing pulse when the intrinsic NF event is not present in the cardiac signal before the interval timer times out.

21. The method of claim 19, wherein the local chamber is a ventricle and the remote EOI represents a P-wave, the method comprising transmitting the FF event marker from the SIMD to direct the LIMD to initiate a PV interval timer as the interval timer, and configuring the LIMD to deliver a ventricular pacing pulse when the LIMD is not inhibited by an intrinsic R-wave before the PV interval timer times out.

22. The method of claim 19, further comprising configuring the SIMD controller to declare an atrial event to occur as the remote EOI in response to detecting an atrial event that exceeds a P-wave sense threshold within a P-wave timing window.

23. The method of claim 19, further comprising configuring the LIMD controller to analyze the cardiac signals and, based thereon, produce a near field (NF) event marker when a local EOI occurs in the local chamber; and wherein the SIMD controller is configured to set a P-wave timing window based on receipt of the NF event marker, the SIMD controller searching for an atrial event during the P-wave timing window.

24. The method of claim 19, further comprising configuring the SIMD to sense P-waves and communicate, as the FF event marker, a P-wave marker indicating detection of the P-waves, to the LIMD; and configuring the LIMD to start a PV interval timer upon detecting the P-wave marker, the LIMD delivering the pacing pulse when an intrinsic R-wave is not detected before the PV interval timer time out.

* * * * *